United States Patent
Dotzel

(10) Patent No.: US 8,575,551 B2
(45) Date of Patent: Nov. 5, 2013

(54) METHOD AND DEVICE FOR MEASURING THE THICKNESS OF A FOUNTAIN SOLUTION LAYER OR INK EMULSION LAYER IN OFFSET PRINTING

(75) Inventor: Klaus-P. Dotzel, Homburg (DE)

(73) Assignee: GVT GmbH, Bad Homburg (DE)

( * ) Notice: Subject to any disclaimer, the term of this patent is extended or adjusted under 35 U.S.C. 154(b) by 272 days.

(21) Appl. No.: 13/092,624

(22) Filed: Apr. 22, 2011

(65) Prior Publication Data
US 2012/0097851 A1    Apr. 26, 2012

(30) Foreign Application Priority Data
Apr. 23, 2010   (EP) ..................................... 10160844

(51) Int. Cl.
*G01J 5/02* (2006.01)
(52) U.S. Cl.
USPC ........................... 250/339.11; 347/19; 356/51
(58) Field of Classification Search
USPC ................. 250/338.1, 339.01, 339.11, 341.8; 347/19; 356/51
See application file for complete search history.

(56) References Cited

U.S. PATENT DOCUMENTS

| | | | |
|---|---|---|---|
| 3,960,451 A | 6/1976 | Wirz et al. | |
| 4,677,298 A | 6/1987 | Zelmanovic et al. | |
| 5,249,036 A | 9/1993 | Balducci | |
| 7,252,360 B2 * | 8/2007 | Hersch et al. | ................... 347/19 |

FOREIGN PATENT DOCUMENTS

| | | |
|---|---|---|
| DE | 24 12 234 B2 | 10/1975 |
| DE | 34 44 784 A1 | 6/1985 |
| DE | 36 11 645 A1 | 10/1987 |
| DE | 691 13 957 T2 | 5/1996 |
| EP | 0 108 889 A2 | 5/1984 |

* cited by examiner

*Primary Examiner* — Mark R Gaworecki
(74) *Attorney, Agent, or Firm* — McDonnell Boehnen Hulbert & Berghoff LLP

(57) ABSTRACT

A method and a device for measuring the thickness of a fountain solution layer or ink emulsion layer on the surface of a cylinder bearing the print image of an offset printing machine is proposed, in which the absorption of reflected near infrared radiation is measured by the dampening water that is applied during print production. Interferences due to optical reflection are eliminated by means of a gloss trap. A position-controlled regulation of the dampening water allocation is reliably maintained by means of machine synchronization of the measuring unit and receiving unit.

16 Claims, 2 Drawing Sheets

Figure 1:
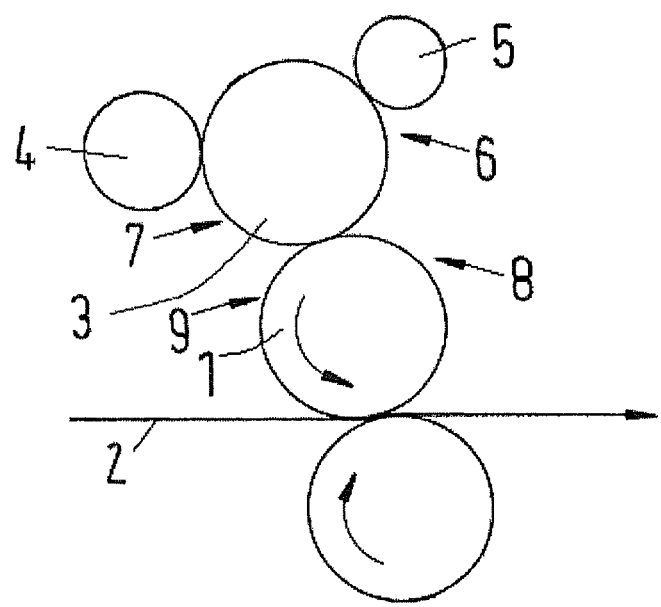

METHOD AND DEVICE FOR MEASURING THE THICKNESS OF A FOUNTAIN SOLUTION LAYER OR INK EMULSION LAYER IN OFFSET PRINTING

CROSS REFERENCE TO RELATED APPLICATIONS

The present application claims priority to EP Patent Application No. 10160844.6, filed Apr. 23, 2010, the entire contents of which are incorporated entirely herein by reference.

The invention concerns a method for measuring the thickness of a fountain solution layer or ink emulsion layer in offset printing, in which the infrared radiation is directed onto the surface of the cylinder bearing the print image and reflected infrared radiation is analyzed.

Further, the invention relates to a device for measuring the thickness of a fountain solution layer and/or ink emulsion layer on the surface of a cylinder that bears the print image with an infrared radiation source that directs infrared radiation onto the surface of the cylinder, and an infrared radiation receiver that receives reflected infrared radiation from the surface of the cylinder, and an analysis unit that is connected with the infrared radiation receiver.

In offset printing it is important to apply a relatively thin and as much as possible evenly distributed fountain solution layer onto the entire surface of the printing plate. The watery fountain solution moistens the non-image-bearing parts of the printing plate and prevents that the oily printing ink is applied at that location. Further, due to the rotation of the cylinder, fountain solution is emulsified into the printing ink and thereby, the rheological and typographical properties are changed. When too much fountain solution, e.g. dampening water is applied, or the fountain solution is unevenly distributed, this leads to disruptions of the ink flow in the inking device and thus to an uneven inking of the printing plate. Further, too much fountain solution influences the dimensional stability of the printing paper which can lead to doubling and to register inaccuracy. When too much fountain solution is used, the drying of the printing inks is also strongly impaired. On the other hand, the amount of fountain solution on the printing plate cannot be reduced arbitrarily, as otherwise, "smearing" and/or "toning" occurs and thereby, non-printing image positions likewise transfer ink.

In practice, the correct adjustment of the printing machine with respect to the fountain solution layer is performed by an experienced printer with the help of specification data. However, such an empirical adjustment is often defective and does not lead to optimal results and to printing difficulties.

For this reason, various ways have already been proposed to determine the thickness of the fountain solution layer, but they have not been accepted in practice. Thus, DE 34 44 784 A1 shows a "Method for monitoring the ink/water relationship in lithographic printing". Here, a beam of light is directed onto the surface of an ink selection roller through a lens, which is reflected subject to predetermined angles. At these various, defined reflection angles, light detectors are mounted that capture the reflected light.

DE 24 12 234 B2 describes a different "Method and device for measuring a fountain solution layer thickness", in which two of the infrared light beams are directed perpendicular onto the printing plate in the form of defined, monochromatic measurement and comparison impulses. An exposure lens at a defined angle captures the reflected radiation.

DE 36 11 645 C2 describes a similar approach for "Controlling ink and fountain solution proportions in an emulsion layer on the printing plate of an offset printing machine". Two different infrared light beams for the ink component and the fountain solution component are directed onto the surface of the printing plate at a defined angle, and the light that is reflected at a right angle to the surface is captured by an exposure lens.

The result is not always satisfactory in every case. The range of the measurement signals is often so large, that the measurement signals are not reliably suitable for controlling the amount of fountain solution.

The invention is based on the problem of reliably measuring the thickness of the fountain solution layer or ink emulsion layer as basis for controlling the complex fountain solution/printing ink system.

This problem is solved by a method of the type mentioned at the beginning thereby, that the infrared radiation is near infrared radiation, preferably in a wavelength range of 700 nm to 2,500 nm, especially preferred less than 2,000 nm, and that a reflected near infrared beam is substantially absorbed by the fountain solution or the ink emulsion as measurement beam, and the other near infrared beam as comparison beam is not substantially absorbed by the fountain solution or by the ink emulsion. According to a preferred embodiment, the measurement beam has a wavelength of approximately 1,930 nm and the comparison beam a wavelength of approximately 1,450 nm.

Due to the comparative measurement of the absorption difference of two monochromatic near infrared wave impulses that primarily differ by their absorption behavior with respect to water, a signal results that has a magnitude which is practically exclusively dependent on the thickness of the fountain solution or ink emulsion layer.

In a further development of the inventive idea, the optical path of the reflected near infrared radiation is directed parallel to the optical path of the emitted near infrared radiation. This means that the reflected radiation falls onto an analysis unit in the opposite direction of the emission.

Preferably, a gloss trap is used at the reflection layer for suppressing reflection errors of the reflected near infrared radiation.

It is assumed, that the large dispersion of the previously found values are due to large fluctuations of intensity at reflecting, moving cylinder surfaces with metallic background. These are eliminated by the gloss trap. Preferably, the gloss trap can also be created by a corresponding geometric arrangement of the transmission and receiving unit relative to the reflecting measurement surface.

In the plane in which the axis of rotation of the cylinder is located, the near infrared radiation, at a predetermined angle that is smaller than 90° with respect to the axis of rotation, is directed to the surface of the cylinder and the reflected near infrared radiation is received at the same angle. This is a relatively simple design for building a gloss trap. It is avoided that directly reflected near infrared radiation is captured by the near infrared radiation receiver. Rather, only that proportion of the diffusely distributed near infrared radiation is received, which is radiated back in the direction of the sender, excluding the mirror reflection. Even though the intensity of the near infrared radiation received thereby becomes smaller, this can in turn be compensated again by corresponding signal amplification. But on the other hand, all influences originating from metallic surfaces and the gloss that is connected with such, or the related reflection, are thus practically completely eliminated.

As a result of the same angle arrangement between emitted and reflected beam relative to the surface of the measurement area, i.e. due to the parallel alignment of the optical paths, a relatively easily verifiable association results between the transmitted and the received near infrared beam.

Preferably, the optical path of the near infrared radiation deviates by 3° to 20° from a plumb line with respect to the surface of the cylinder. At this range of angle it is ensured that even diffusely reflected or reflected near infrared radiation still has sufficient strength to be able to obtain a suitable signal strength for determining a parameter.

Alternatively or in addition to the angular arrangement of the near infrared radiation sources and radiation receivers, a polarization filter can also be used as gloss trap. The polarization filter is then aligned in such a way that it eliminates those effects that come from gloss or optical reflection. The polarization filter, for example, lets only those waves of the near infrared radiation pass through that propagate in a plane in which the axis of rotation is located. This also ensures that the parameter is obtained exclusively due to the diffusely reflected near infrared radiation from the surface of the cylinder.

In preferred manner, a comparative analysis of the measurement and comparative radiation is done only on at least one predetermined section of the surface. This means that the measurement can either be performed at least on one defined measurement section of the plate cylinder that bears the printing plate on at least one measuring position, or the measurement can be performed on at least one defined measurement section of the rubber cylinder, at least on one measurement position.

Thereby, a clearly defined measurement position is given, at which the other relationships are always the same. If something changes here, it can only be the thickness of the dampening water layer. This makes the analysis easier.

Preferably, the section is a non-printing section or a defined printing section (full tone or defined grid pattern) on a cylinder that bears the print image. A non-printing section is a section at which no printing ink is transferred. This section is moistened by the fountain solution layer, but it does not absorb any ink. At such a non-printing section, the thickness of the fountain solution layer can therefore be determined relatively reliably. In contrast, a printing measurement section is a section in which the ink is transferred to the entire surface, or transferred onto the medium that is to be printed with a defined grid. Here, the thickness of the ink emulsion layer can be measured by the water content.

Preferably, the reflection values of both near infrared beams are analyzed using defined measurement positions. The exact position in the operating direction of the printing machine occurs by synchronization of the near infrared measurement units with the printing machine by means of a rotation angle sender. Horizontal to the operating direction of the machine, the positioning occurs by means of a traverse parallel to the axis of the cylinder on which the transmitting and receiving units are mounted. In this way it is ensured that always only the same section is used for the analysis.

Preferably, a first monochromatic near infrared beam and a second monochromatic near infrared beam are used, whereby the near infrared beams are directed to the surface simultaneously or sequentially. The wave lengths are in the near infrared range (near infrared range) and are, according to the invention, in the range of approximately 700 nm to approximately 2,500 nm, especially preferred in the range of less than 2,000 nm. In this case, one of the two beams is used as comparison beam and the second as measuring beam for the absorption by the dampening water.

If on the one hand both beams are simultaneously directed to the measuring position, the two reflected beams must be captured correspondingly separated by using two receivers. This means, the measurement occurs due to simultaneously emitted near infrared beams with different wavelengths simultaneously at the at least one measuring position—synchronous with the speed of rotation of the cylinder that bears the print image—and the reflected near infrared beams are captured by a wavelengths-selective detector, for example, by prisms, grids or diode arrays.

Preferably, the method can be applied on the other hand in such a way that the measurement due to sequentially emitted near infrared beams with different wavelengths occurs chronologically offset at the at the at least one measuring position—synchronous with the speed of rotation of the cylinder that is bearing the print image—and the reflected near infrared beams are captured by a joint near infrared beam receiver.

The sequentially emitted near infrared beams can, for example, be generated by a machine-synchronized change of filters or emitters. Then, a sequentially working near infrared radiation receiver is sufficient for the analysis. This is always possible then, when no significant changes in the fountain solution layer are to be expected between individual rotations of the cylinder. Due to the relative measurement, the differences caused by contamination of the dampening water, or by different printing plate surfaces are eliminated.

Preferably, the calibration of the absorption difference with respect to the dampening water layer strength is performed by using a suitable absorption filter.

Preferably, the measured thickness of the layer is used for controlling the application of the fountain solution. As therefore, a measured value with sufficient reliability is now available, it can be used for controlling the dampening units and the effective amounts of printing ink subject to the production conditions for printing.

The same angle arrangement between emitted and reflected near infrared radiation makes it easier to measure the thickness of the layer by compensating interfering effects such as fluctuations of the ambient relationships, and simplifies analysis.

The problem of the present invention is solved by a device of the type mentioned at the beginning thereby, that the device comprises an optical measurement system with a near infrared radiation source for generating emitted near infrared radiation and a near infrared radiation receiver for receiving reflected near infrared radiation, whereby the optical paths of the emitted near infrared radiation and the reflected near infrared radiation are parallel to each other. In addition, the device comprises an analysis unit that is connected with the optical measurement system for analyzing the data transmitted by the near infrared radiation receiver. The device according to the invention is suitable particularly for performing the method according to the invention.

Optionally, the optical measurement system has a near infrared radiation source and a near infrared radiation receiver surrounded by a housing.

Preferably, the device can further be provided with a filter wheel with preferably two windows that are provided with various wavelengths-selective filters in the optical path of the emitted near infrared radiation, and a synchronization unit that is connected with the filter wheel and the cylinder that bears the print image.

Alternative to that or additionally, the optical measurement system of the device can further have at least one grid, a prism or a near infrared diode array in the optical path of the reflected near infrared radiation.

The structural design is simplified by reducing the need for space and due to the installation possibilities. As a rule, only relatively little space is available in an offset printing machine in order to house the devices required for measurement. It is advantageous when the emitted and reflected near infrared radiation is transmitted in one or two light wave guides that extend parallel from the light source to the measurement position and from the measurement position to the near infrared receiver. In this case, the installation size at the measurement position is minimized and the transmitting, receiving and analysis unit can be mounted outside of the working area at the plate cylinder, at a distance from the measurement position.

It is also advantageous when the near infrared radiation source and the near infrared radiation receiver—these can also only be the ends of the light wave guide—is mounted so it can be positioned variably on a mounting device such as a traverse that is directed parallel to the axis of rotation of the cylinder. In combination with the synchronization of the printing machine the possibility results that all printing plates mounted at all suitable positions of a printing plate, and/or several adjacently mounted printing plates on a printing cylinder, can be monitored and partially controlled with one measurement unit.

It is especially preferred when in the device for measuring the thickness of the fountain solution layer or ink emulsion layer, glass materials are used as optic material and a compact light wave guide installation is used. This offers advantages, in particular in the critical machine sector of offset printing, in which high speeds of rotation of the plate cylinder and rubber cylinder occur of approximately 15 m/s. In addition, the use of light wave guides facilitates safe operation during plate changes and is considered to be advantageous with respect to contamination by ink and fountain solution.

The use of light wave guides is preferably limited to wavelengths below 2,000 nm, as a transmission over a required length of about 3 m would not be possible due to the internal damping of the light wave guides.

Figure 2:
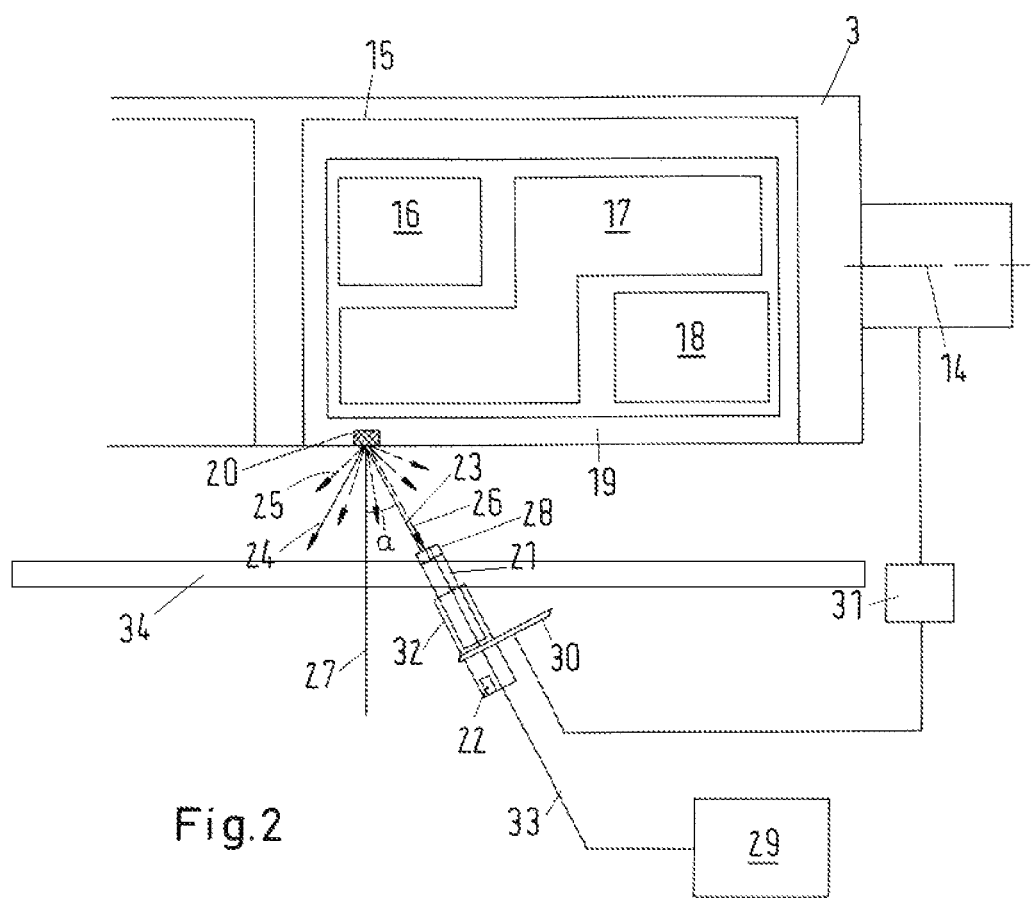

Additional goals, characteristics, advantages and applications result from the following description of the examples of embodiments of the invention with the help of the figures. Thereby, all described and/or illustrated characteristics by themselves, or in any combination form the subject matter of the invention, even independent of their abstracts in the claims or their reference. Shown are:

FIG. 1 a schematic illustration of a printing unit in an offset printing machine and FIG. 2 a schematic illustration of a device for measuring the thickness of a fountain solution layer or ink emulsion layer on a cylinder that bears the print image of an offset printing machine.

FIG. 1 shows a highly schematic illustration of a printing unit of an offset printing machine—not shown in further detail—for printing a paper web 2.

The printing unit has a plate cylinder 3 that bears a printing plate 15. The printing plate 15 defines the print image that appears later on paper web 2. By means of a dampening unit 4 dampening water (or another dampening agent) is transferred to printing plate 15. An inking device 5 is used for inking the printing plate 15 of plate cylinder 3. The inked print image of the printing plate 15 is transferred to the paper web 2 by a rubber cylinder 1. In principle, this type of setup is known.

The possible measurement positions 20 for measuring dampening water on the plate cylinder 3 that bears printing plate 15 are labeled with 6 and 7, those on the rubber cylinder 1 with 8 and 9.

Plate cylinder 3 is shown schematically in FIG. 2. Several printing plates 15 are mounted on plate cylinder 3 (only one is shown). On printing plate 15, printing sections 16 to 18 and non-printing sections 19 are provided. By means of the inking unit 5, ink is transferred to the printing sections 16 to 18 of printing plate 15. By means of dampening unit 4, the fountain solution is transferred to the non-printing sections 19 so that these sections 19 remain free of ink. In this process, the dampening water is emulsified into the ink. The print image is transferred by the printing plate 15 to rubber cylinder 1 and from there to paper web 2. Correspondingly, the plate cylinder 3 that bears the printing plate 15, and also rubber cylinder 1, is a cylinder that bears a print image.

On printing plate 15, the printing sections 16 to 18 are designed as oleophilic and hydrophobic sections. In contrast, the non-printing sections 19 are hydrophilic and oleophobic. Correspondingly, an ink-fountain-solution emulsion is formed by oil-based printing ink and dampening water, which is applied to the printing sections 16 to 18 of printing plate 15. In contrast, the dampening water moistens the non-printing sections 19 so that the oily printing ink emulsion is rejected there.

The applied thickness of the dampening water layer is to be adjusted as precisely as possible. As a rule, it is between 1 µm and 6 µm. A dampening water layer that is too thick leads to higher dampening water content in the ink emulsion, which leads to ink separation with low ink transfer in printing. In contrast, a dampening water content that is too low leads to ink separation with higher ink transfer, up to inking the non-printing sections during printing.

To measure the thickness of the dampening water layer, at least one measuring position 20 (and/or 6, 7, 8, 9) is defined on the at least one printing plate 15. The measuring position 20 is located in the non-printing section 19, i.e. there, where no ink is to adhere, but only dampening water. Alternatively, the measuring position 20 can also be provided at rubber cylinder 1. In both cases, the thickness of the layer of dampening water can be measured. In contrast, if the thickness of the ink emulsion layer is to be measured, a measuring position (not shown in more detail) is used by means of which ink is transferred to the entire surface.

An optical measurement system 21 is mounted on a traverse 34 so that it can be positioned variably—with which several measuring positions 20 and/or 6, 7, 8, 9 and printing plates can be actuated exactly horizontal to the axis of the cylinder. In the axial direction of cylinder 3, different measuring positions 20 can be actuated and there, the thickness of the dampening water layer or the ink emulsion layer can be measured respectively without requiring several measuring systems of this type.

The actuation of the measuring positions 20 (and/or 6, 6, 8, 9) occurs in the direction of operation of the printing machine by the speed sensor position of the synchronization unit 31. Simultaneously, the synchronization unit 31 controls the changing near infrared measurement by means of filter wheel 30.

The optical measurement system 21 has a near infrared radiation source 22, which directs near infrared radiation 23 to measuring position 20. The near infrared beams 23 are reflected there, as shown by an arrow 24, according to the law of "angle of incidence=emergent angle", by measuring position 20. In addition, diffusely reflected near infrared radiation is generated, which is illustrated by dotted-line arrows 25, 26. The near infrared beams 23 lie in a plane in which the axis of rotation 14 is also located. Beyond that, together with the axis of rotation 14 they form an angle≠90°. For a better explanation, a plane 27 is shown, on which axis of rotation 14 is perpendicular. The near infrared beams 23 form an angle α with this plane 27 in the range of 3° to 20°, so that the near infrared beams 23 form an angle in the range of 70° to 87° with axis of rotation 14, and mirror reflection is avoided.

The optical measurement system 21 has a near infrared radiation receiver 28, which receives diffusely reflected near infrared radiation 26 that lies at the same angle to the measurement position 20 as the emitted near infrared beams 23.

The near infrared radiation receiver 28 is connected with an analysis unit 29. The analysis unit 29 in turn—in a way that is not shown in further detail—is connected with the dampening unit 4, to control the amount of the dampening water that is applied in such a way that the applied dampening water layer and the transferred printing ink emulsion layer have defined thickness.

For precise positioning of the measurement on the cylinder 1, 3 bearing the print image, the near infrared radiation source 22 emits its near infrared radiation through a filter wheel 30, that is rotated depending on the rotation of the cylinder 1,3 bearing the print image. For this, a synchronization unit 31 is provided in highly schematic illustration. The filter wheel 30 has two windows that are provided with various wavelength-selective filters, so that alternately a near infrared beam 23a with a near infrared measurement wave length that is to be absorbed, and a near infrared beam 23b with a near infrared comparison measurement wavelength that is not to be absorbed are directed to measuring position 20. The absorption of the near infrared measurement wave length in the fountain solution layer or ink emulsion layer depends on the thickness of the layer, while the near infrared comparison wavelength remains substantially unaffected by it. By means of a comparison of the diffusely reflected near infrared measurement beam 23a and the standardization of the diffusely reflecting near infrared comparison beam 23b, the thickness of the dampening water layer can then be determined.

Between the two windows with the respective monochromatic filters, the near infrared radiation source 22 is covered. Hereby, the rotation of the filter wheel 30 is synchronized with the rotation of the plate cylinder 3 in such a way that one window is released always then, when the near infrared beam impinges on the measurement position 20. The wavelengths of the near infrared beams are in the range of 700 nm to 2,500 nm, i.e. they are in the near infrared range (NIR range).

Die near infrared radiation source 22 and the near infrared radiation receiver 28 are advantageously located in the same housing 32. Hereby, a device is considered to be the near infrared radiation source 22 when it emits near infrared radiation. Thereby, this can by all means also be the facing side of a light guide, the other side of which is supplied with near infrared radiation. This has the advantage that the actual generation of the near infrared radiation can be done at that location where sufficient space is available. The light guide—not shown in further detail—can then perform the "transport" of the near infrared radiation to the measurement site. In the same way, the near infrared radiation receiver 28 is also understood as that location, at which the near infrared radiation is received.

Alternatively, or in addition to the angled arrangement of the optical measurement system 21—in a way that is not illustrated further—a polarization filter can also be used.

With both approaches, the effect of a "gloss trap" is created with the help of which high fluctuations of intensity of reflecting, moving cylinder surfaces with metallic background can be avoided.

REFERENCE NUMBERS

1 Rubber cylinder
2 Paper web
3 Plate cylinder
4 Dampening unit
5 Inking unit
6, 7 Measurement position (on the plate cylinder)
8, 9 Measurement position (on the rubber cylinder)
14 Axis of rotation of the cylinder bearing the print image
15 Printing plate
16, 17, 18 Printing section
19 Non-printing section
20 Measurement position
21 Optical measurement system
22 Near infrared radiation source
23 Near infrared beam
24 Mirror reflection—reflected near infrared beam
25, 26 Diffusely reflected near infrared beam
27 Plane
28 Near infrared radiation receiver
29 Analysis unit
30 Filter wheel
31 Synchronization unit
32 Housing
33 Light wave guide
34 Traverse

The invention claimed is:

1. Method for measuring the thickness of a fountain solution layer or ink emulsion layer on a cylinder bearing a print image of an offset printing machine,
    in which two monochrome infrared beams with different wave lengths are directed simultaneously or sequentially onto at least one defined measurement position and are reflected there,
    whereby the reflected radiation is captured in an analysis unit,
    wherein the infrared beams are near infrared beams and that the one reflected near infrared beam is substantially absorbed by the fountain solution or the ink emulsion as measurement beam, and
    the other near infrared beam as comparison beam is not substantially absorbed by the fountain solution or by the ink emulsion.

2. Method according to claim 1,
    wherein the optical path of the reflected near infrared radiation is arranged parallel to the optical path of the emitted near infrared beam.

3. Method according to claim 1,
    wherein when measuring the reflected near infrared radiation a gloss trap is used.

4. Method according to claim 3,
    wherein the at least one gloss trap is formed by a suitable geometric arrangement of the emitted near infrared radiation and
    the reflected near infrared radiation is formed on the at least one measurement position, by locating both optical paths outside of the mirror reflection.

5. Method according to 3,
    wherein the at least one gloss trap is formed by a polarizer.

6. Method according to claim 1,
    wherein a measurement on at least one defined measurement section of a plate cylinder bearing a print plate is performed on at least one measurement position.

7. Method according to claim 1,
    wherein a measurement on at least one defined measurement section of a rubber cylinder is performed on at least one measurement position.

8. Method according to claim 1
    wherein the measurement section comprises a non-printing section or a printing section.

9. Method according to claim 1,
wherein the measurement is either chronologically offset by sequentially emitted near infrared beams of different wavelengths on the at least one measurement position synchronous with the speed of rotation of the cylinder bearing the print image, and
the reflected near infrared beams are captured by a joint near infrared radiation receiver, or is performed by simultaneously emitted near infrared beams of different wavelength simultaneously on the at least one measurement position synchronous with the speed of rotation of the cylinder bearing the print image, and
the reflected near infrared beams are captured by a wavelength-selective detector.

10. Method according to claim 1,
wherein the measured layer thickness is used for position-controlled regulation of the application of the fountain solution or the ink emulsion.

11. Device for measuring the thickness of a fountain solution layer or an ink emulsion layer on a cylinder bearing a print image of an offset printing machine, the device comprising:
an optical measurement system comprising a near infrared radiation source for generating emitted near infrared radiation and a near infrared radiation receiver for receiving reflected near infrared radiation,
whereby the optical paths of the emitted near infrared radiation and the reflected near infrared radiation are parallel to each other, and
an analysis unit operatively coupled to the optical measurement system for analyzing the data transmitted by the near infrared radiation receiver.

12. Device according to claim 11,
wherein the optical measurement system comprises a filter wheel with preferably two windows,
which have different wavelength-selective filters in the optical path of the emitted near infrared radiation and a synchronization unit,
which is connected with a filter wheel and with the cylinder bearing the print image.

13. Device according to claim 11,
wherein the optical measurement system further comprises at least one grid, a prism or a near infrared diode array in the optical path of the reflected near infrared radiation.

14. Device according to claim 11,
wherein the device further comprises a mounting device, at which the optical measurement system is mounted
and that the mounting device lies in a plane with the axis of rotation of the cylinder bearing the print image.

15. Device according to claim 14,
wherein the optical measurement system is positioned variably.

16. Device according to claim 11,
wherein the device further comprises at least one light wave guide that leads from the near infrared radiation source to the at least one measurement position, and
from the at least one measurement position to the near infrared radiation receiver.

* * * * *